(12) United States Patent
Larsen et al.

(10) Patent No.: US 10,137,254 B2
(45) Date of Patent: Nov. 27, 2018

(54) TELESCOPIC DRIVE ARRANGEMENT FOR DRUG DELIVERY DEVICE

(71) Applicant: Novo Nordisk A/S, Bagsvaerd (DK)

(72) Inventors: Bjoern Gullak Larsen, Birkeroed (DK); Carsten Schau Andersen, Valby (DK); Jesper Hoeholt, Melby (DK); Finn Hougaard, Koebenhavn K (DK)

(73) Assignee: Novo Nordisk A/S, Bagsvaerd (DK)

( * ) Notice: Subject to any disclaimer, the term of this patent is extended or adjusted under 35 U.S.C. 154(b) by 93 days.

(21) Appl. No.: 15/307,652

(22) PCT Filed: Apr. 29, 2015

(86) PCT No.: PCT/EP2015/059384
§ 371 (c)(1),
(2) Date: Oct. 28, 2016

(87) PCT Pub. No.: WO2015/165992
PCT Pub. Date: Nov. 5, 2015

(65) Prior Publication Data
US 2017/0143909 A1    May 25, 2017

(30) Foreign Application Priority Data
May 2, 2014   (EP) ..................... 14166859

(51) Int. Cl.
*A61M 37/00*   (2006.01)
*A61M 5/315*   (2006.01)
(Continued)

(52) U.S. Cl.
CPC .......... *A61M 5/31583* (2013.01); *A61M 5/24* (2013.01); *A61M 5/31501* (2013.01);
(Continued)

(58) Field of Classification Search
CPC ................ A61M 5/31583; A61M 5/24; A61M 5/31546; A61M 39/10
(Continued)

(56) References Cited

U.S. PATENT DOCUMENTS 2,598,528 A  5/1952  French
5,693,027 A  12/1997  Hansen et al.
(Continued)

FOREIGN PATENT DOCUMENTS

DE  804455 C  4/1951
EP  226764 A2  7/1987
(Continued)

*Primary Examiner* — Phillip Gray
(74) *Attorney, Agent, or Firm* — Wesley Nicolas (57) ABSTRACT

Drug delivery device adapted to receive a cartridge, comprising a drive tube with an inner thread, a motor assembly comprising a drive shaft and being adapted to be received inside the drive tube, a drive member attached to the drive shaft and with an outer thread in engagement with the drive tube inner thread. The drive tube is arranged axially displaceable but non-rotational relative to the motor assembly, whereby rotation of the drive member results in axial, non-rotational displacement of the drive tube. To provide flexibility the drive shaft is connected to the drive member via a first flexible joint, and the motor assembly proximal portion is connected to a support structure via a second flexible joint.

7 Claims, 9 Drawing Sheets

(51) Int. Cl.
*F16H 25/20* (2006.01)
*A61M 5/24* (2006.01)
*A61M 39/10* (2006.01)

(52) U.S. Cl.
CPC .... *A61M 5/31513* (2013.01); *A61M 5/31546* (2013.01); *A61M 39/10* (2013.01); *F16H 25/20* (2013.01); *A61M 2005/2481* (2013.01); *A61M 2005/31518* (2013.01); *A61M 2005/31588* (2013.01); *A61M 2039/1022* (2013.01); *A61M 2205/14* (2013.01); *A61M 2205/581* (2013.01); *A61M 2205/583* (2013.01); *A61M 2205/8206* (2013.01); *F16H 2025/2075* (2013.01)

(58) Field of Classification Search
USPC .......................................................... 604/155
See application file for complete search history.

(56) References Cited

U.S. PATENT DOCUMENTS

| | | |
|---|---|---|
| 6,004,297 A | 12/1999 | Steenfeldt-Jensen et al. |
| 6,171,286 B1 | 1/2001 | Gross |
| 6,514,230 B1 | 2/2003 | Munk et al. |
| 6,854,620 B2 | 2/2005 | Ramey |
| 7,073,406 B2 | 7/2006 | Garrec |
| 7,703,377 B2 | 4/2010 | Mintgen et al. |
| 2009/0036846 A1 | 2/2009 | Dacquay et al. |
| 2009/0093792 A1 | 4/2009 | Gross et al. |
| 2011/0306927 A1 | 12/2011 | Watanabe et al. |
| 2012/0184917 A1 | 7/2012 | Bom et al. |
| 2013/0304021 A1 | 11/2013 | Cabiri et al. |
| 2017/0007774 A1 | 1/2017 | Brockmeier |
| 2017/0175859 A1 | 6/2017 | Brockmeier |

FOREIGN PATENT DOCUMENTS

| | | | |
|---|---|---|---|
| EP | 1801457 A1 | 6/2007 | |
| EP | 2140897 A1 | 1/2010 | |
| EP | 2332600 A1 | 6/2011 | |
| EP | 2335755 A1 | 6/2011 | |
| EP | 14159913.4 | 5/2014 | |
| FR | 2884722 A1 | 10/2006 | |
| GB | 2044879 A | 10/1980 | |
| WO | 9700091 | 1/1997 | |
| WO | 0234315 A1 | 5/2002 | |
| WO | 03099357 | 12/2003 | |
| WO | WO 03099357 A1 * | 12/2003 | ........ A61M 5/14566 |
| WO | 2010076792 A1 | 7/2010 | |
| WO | 2013/124119 A1 | 8/2013 | |
| WO | 2013/144152 A1 | 10/2013 | |

* cited by examiner

TELESCOPIC DRIVE ARRANGEMENT FOR DRUG DELIVERY DEVICE

CROSS-REFERENCE TO RELATED APPLICATIONS

This application is a 35 U.S.C. § 371 National Stage application of International Application PCT/EP2015/059384 (published as WO 2015/165992), filed Apr. 29, 2015, which claims priority to European Patent Application 14166859.0, filed May 2, 2014; the contents of which are incorporated herein by reference.

The present invention generally relates to a telescopic drive mechanism. In a specific aspect the invention relates to a motorized drug delivery device adapted to receive a drug filled cartridge and subsequently expel a dose therefrom.

BACKGROUND OF THE INVENTION

In the disclosure of the present invention reference is mostly made to the treatment of diabetes by subcutaneous drug delivery, however, this is only an exemplary use of the present invention.

The most common type of durable drug delivery devices adapted to receive a drug filled cartridge and expel a set dose therefrom are driven by manual means or by a spring energized during dose setting, the cartridge being of the type comprising an axially displaceable piston having an initial proximal position and which is moved distally by a piston rod. Subcutaneous drug delivery takes place via an injection needle arranged in fluid communication with the cartridge. The device may be pen-formed or in the form of a more box-shaped so-called doser. In order to improve convenience, user-friendliness and provide additional features, e.g. detection and storing of expelling data, drug delivery devices have been provided with electrically driven means, typically in the form of an electronically controlled motor driving a piston rod through a gear arrangement, e.g. as shown in U.S. Pat. No. 6,514,230 and US 2011/306927.

Although motorized drug delivery devices facilitate a number of benefits to the customer as many trivial routines can be automated, these devices are often rather large in comparison to conventional mechanical devices and thus they are impractical to carry and store. Addressing this issue WO 03/099357 discloses a pen-formed drug delivery device comprising a drive arrangement including a piston rod in the form of a tubular body that can be moved into a drug cartridge when being advanced in a distal direction, the tubular body defining an internal hollow wherein at least a portion of a motorized drive assembly is arranged when the tubular body is positioned in a retracted proximal position. This configuration for a drive assembly may be termed "motor-in-piston". Such a drive assembly could also be considered a telescopic drive assembly in which the inner motor drive assembly is the stationary part and the outer tubular body is the moved telescopic part.

Although a motor-in-piston design may result in a compact design, the design involves a number of moving components which interface with multiple other components, all being arranged in a confined space. Such a design will often result in a mechanical design in which the components involved are over-constrained which in turn can lead to malfunction of the device and/or increased production cost and lower production yield.

Having regard to the above, it is an object of the present invention to provide a motorized drug delivery device of the motor-in-piston type as well as components therefor which provide a high degree of reliability in a cost-effective way. It is a further object to provide a general-purpose telescopic drive assembly which is compact in design and provides a high degree of reliability in a cost-effective way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery device is provided comprising a compartment adapted to receive and hold a drug-filled cartridge having an axially moveable piston. The device further comprises a support structure, a drive tube with an inner thread, a motor assembly having a distal portion and a proximal portion, the distal portion comprising a rotatable drive shaft and being adapted to be received inside the drive tube, a drive member comprising an outer thread, and a controller for controlling the motor assembly. The drive tube is arranged axially displaceable but non-rotational relative to the motor assembly, the drive tube being adapted to engage and axially move, directly or indirectly, the piston of a loaded cartridge to thereby expel drug from the cartridge, and the motor assembly is arranged non-rotational relative to the support structure. The drive member outer thread is in threaded engagement with the drive tube inner thread, whereby rotation of the drive shaft results in axial, non-rotational displacement of the drive tube relative to the support structure. The motor assembly proximal portion is connected to the support structure via a first flexible joint, and the drive shaft is connected to the drive member via a second flexible joint. The flexible joints may for example be in the form of a universal joint, a helical spring or an Oldham coupling, either the same or different.

By providing a drive assembly with flexible joints the motor assembly is allowed to move, e.g. flex or "wobble", relative to the chassis, just as the drive member together with the drive tube is allowed to move, e.g. flex or "wobble", relative to the motor assembly and thus also the chassis, the arrangement yet still providing the desired transmission of rotation, this allowing a cost-effective design requiring less restrictive tolerances for the involved components. Alternatively, considering e.g. design, cost or space issues, only one of the flexible joints may be incorporated in the drive assembly design.

In an exemplary embodiment the drive shaft defines a general axis, and the first and second flexible joints are configured to prevent rotation and axial movement relative to the general axis between the motor assembly proximal portion and the support structure respectively between the drive shaft and the drive member.

The controller and motor assembly may be adapted to move the drive tube in a distal direction to thereby expel drug from a loaded cartridge, and move the drive tube in an opposed proximal direction to thereby retract the drive tube from a loaded cartridge. Setting means allowing a user to set a dose of drug to be expelled may be provided.

The drug delivery device may comprise a rechargeable electric power source, and an electrical connector allowing an external connector of a power source to be connected for recharging the power source, wherein the controller is adapted to detect a condition indicative of an external power source being connected to the electrical connector and subsequently disable the expelling assembly to thereby prevent that drug can be expelled from a loaded cartridge when an external power source has been connected to the electrical connector.

In an alternative configuration, a general-purpose telescopic drive assembly is provided, comprising a drive tube comprising an inner thread, and a motor assembly having a distal portion and a proximal portion, the distal portion comprising a rotatable drive shaft being adapted to be received inside the drive tube. The drive assembly further comprises a drive member with an outer thread in threaded engagement with the drive tube inner thread, the drive member being connected to the drive shaft, and a mounting structure adapted to mount the motor assembly non-rotationally relative to a support structure. The drive tube is adapted to be arranged axially displaceable but non-rotational relative to the motor assembly, whereby rotation of the drive shaft results in axial, non-rotational displacement of the drive tube relative to the motor assembly and thus the support structure. The drive shaft is connected to the drive member via a first flexible joint, and the motor assembly proximal portion is connected to the mounting structure via a second flexible joint. The assembly may be provided in combination with the supporting structure. The drive assembly may further comprise at least portions of controller circuitry for controlling the motor assembly.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs, this including analogues thereof as well as combinations with one or more other drugs.

BRIEF DESCRIPTION OF THE DRAWINGS

In the following exemplary embodiments of the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to a detailed description of an exemplary embodiment of the invention a schematic representation of drug delivery device with a telescopic motor-in-piston drive assembly will be described to better provide an understanding of the general working principle of such an arrangement.

Figure 1:
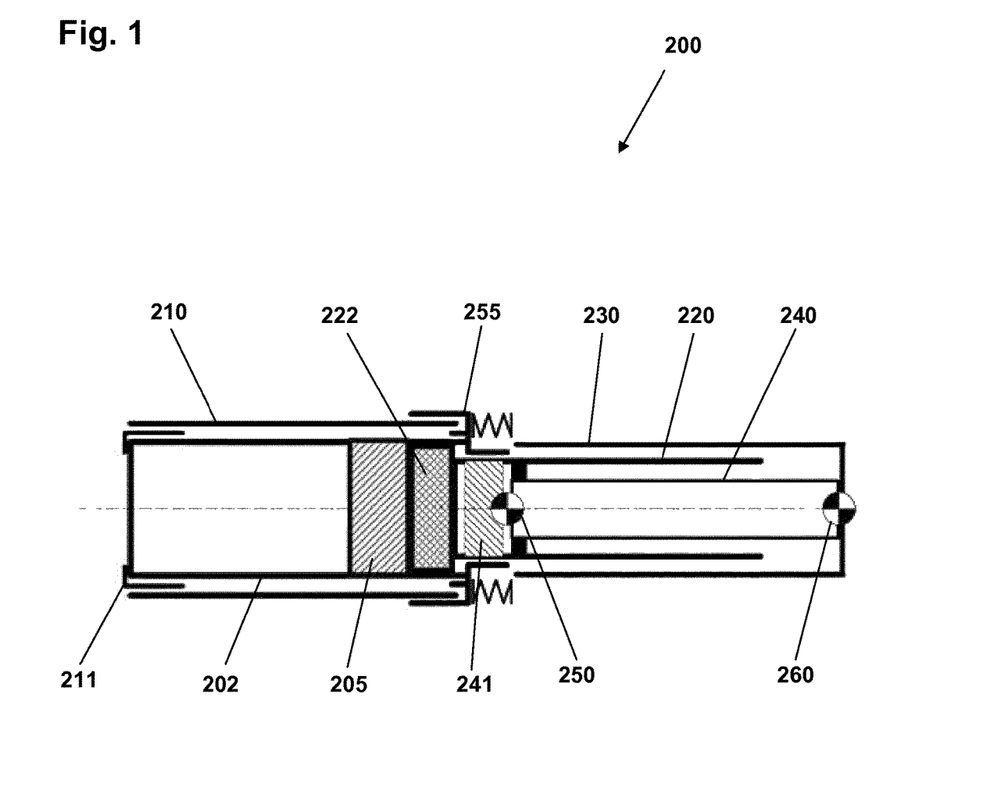
FIG. 1 shows schematically a first embodiment of a drug delivery device incorporating a motor-in-piston drive assembly.

More specifically, FIG. 1 shows schematically a first embodiment of an exemplary drug delivery device 200 comprising a front-loaded compartment portion 210 adapted to receive and hold a drug-filled cartridge 202 by means of distally arranged cartridge holding means 211, a main portion 230 in which a telescopic motor-in-piston drive assembly 220, 240 is arranged, and a bias assembly 255 providing a biasing distally directed force on a loaded cartridge. The compartment portion and the main portion may be rotationally or rigidly connected to each other. The main portion may provide or accommodate a support structure for other components of the device, e.g. in the form of a chassis or platform.

The drive assembly comprises an outer piston drive tube 220 with an inner thread, a motor-gear assembly 240 having a distal portion and a proximal portion, the distal portion comprising a rotatable drive shaft defining a z-axis and to which is mounted a drive member 241 comprising an outer thread in engagement with the piston drive tube inner thread. The motor-gear assembly is arranged axially non-displaceable and non-rotational relative to the chassis, the drive member is mounted axially non-displaceable and non-rotational on the drive shaft, and the piston drive tube is arranged axially displaceable but non-rotational relative to the chassis 230 and thus also to the motor assembly, whereby rotation of the drive shaft results in axial, non-rotational displacement of the piston drive tube relative to the chassis, the piston drive tube being adapted to engage and axially move distally, directly or indirectly, the piston of a loaded cartridge to thereby expel drug from the cartridge. In the shown embodiment the piston drive tube is provided with a distal drive head 222 adapted to engage the piston 205 of a loaded cartridge 202.

For proper function of a telescopic drive assembly all interfaces must remain free to translate and/or rotate along relatively long distances as the outer tube is driven forward for which reason small tolerances on components may be required to ensure that the components maintain movability. Additionally, it may be desirable to keep the dimensions of the telescopic drive assembly as small as possible by minimizing clearance between components. This can require additionally small component tolerances.

Addressing these issues the shown embodiment of FIG. 1 provides special kinematic joints to allow additional degrees of freedom between components. More specifically, the drive shaft is connected to the drive member via a first flexible joint 250, and the motor-gear assembly proximal portion is connected to the chassis via a second flexible joint 260, the flexible joints being designed to provide a rotational lock between the connected components, yet allowing the components to bend or flex relative to each other.

Figure 2:
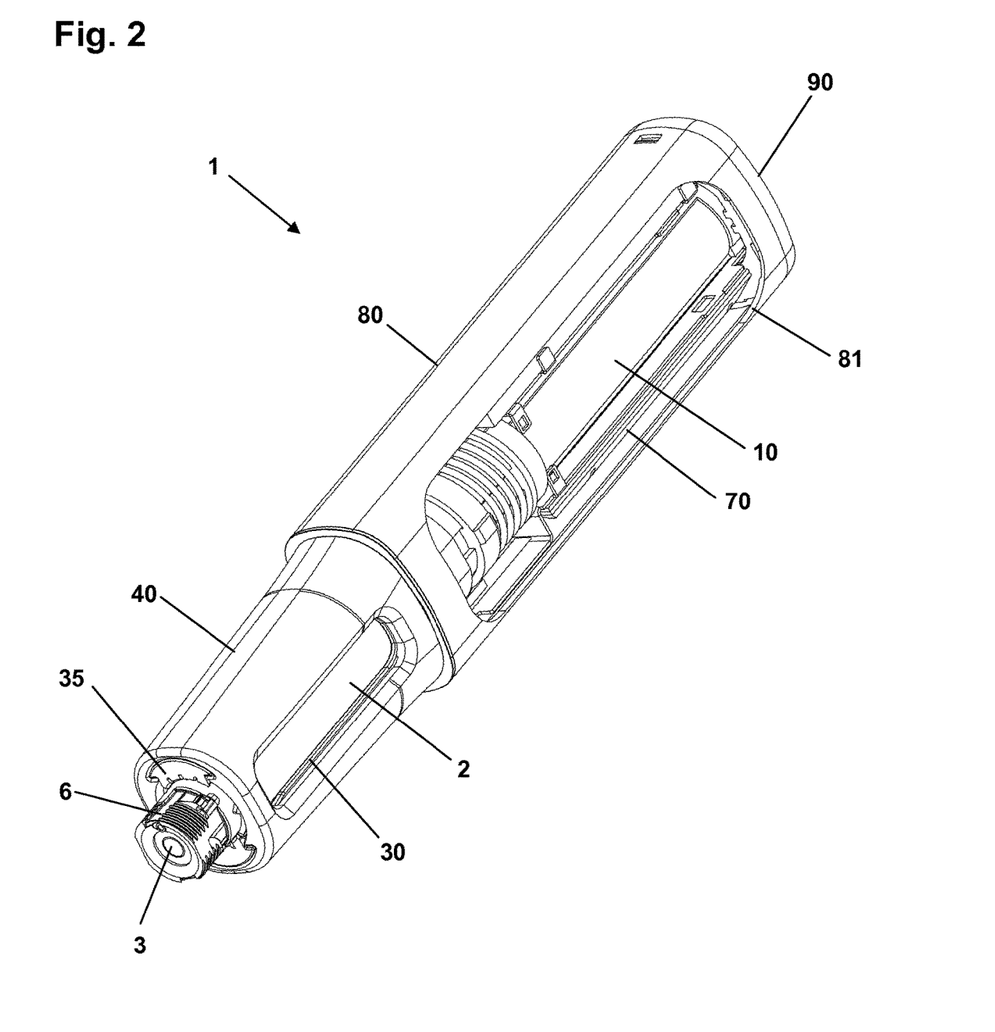
FIG. 2 shows a front-loaded motorized drug delivery device incorporating a motor-in-piston drive assembly.

Referring to FIG. 2 a more detailed embodiment of a motorized pen-formed drug delivery device incorporating a motor-in-piston drive assembly will be described.

More specifically, the pen device comprises a cap part (not shown) and a main part having a proximal body or drive assembly portion 2 with a housing 80 in which a drug expelling mechanism and associated electronics 70 are arranged, and a distal cartridge holder portion 30, 40 forming a compartment 41 (see FIG. 8) in which a drug-filled transparent cartridge 2 can be arranged and retained in place by a cartridge holder assembly mounted to the proximal portion. The housing comprises an opening 81 adapted to receive a display frame member (not shown) in which a LCD as well as user input keys are mounted. With the frame member removed portions of the motorized expelling mechanism 10 and the electronic components 70 can be seen. A pair of dose setting input keys (not shown) serves to manually set a desired dose of drug shown in the LCD and which can then be expelled when a proximally arranged release button 90 is actuated. The device is designed to be loaded by the user with a new cartridge through a distal receiving opening in the cartridge holder assembly.

The cartridge comprises a cylindrical body portion, a distal outlet portion with a distal needle-penetrable septum 3, a proximal open-ended portion with a circumferential rim 4, and an axially displaceable piston 5 (see FIG. 7) having a proximal surface allowing a piston driver forming part of the expelling mechanism (see below) to engage the piston. The cartridge may for example contain an insulin, a GLP-1 or a growth hormone formulation. The cartridge is provided with distal coupling means in the form of a needle hub mount 6 having, in the shown example, combined thread and bayonet coupling means, each being adapted to engage an inner thread or bayonet coupling means of a corresponding hub of a needle assembly. The shown exemplary hub mount further comprises a circumferential flange with a number of distally facing pointed projections serving as a coupling means for the cartridge holder assembly as will be described in more detail below. A hub mount of the shown type is described in U.S. Pat. No. 5,693,027. Alternatively the needle hub mount may be formed as part of the cartridge holder, e.g. in the form of a "split" hub mount having two parts arranged on each side of the gripping shoulders, see below.

As shown, the cartridge holder assembly has the same general appearance as a traditional cartridge holder which is detachably coupled to the housing by e.g. a threaded coupling or a bayonet coupling and into which a new cartridge can be received as well as removed through a proximal opening, i.e. it comprises no additional user operated release or locking means. Instead, what appears merely to be the cartridge holder per se is in fact user operated coupling means in the form of an outer rotatable tubular actuation sleeve 40 operated by the user to control movement of cartridge holding means in the form of an inner cartridge holder member 30 to thereby open and close gripping shoulders 35 configured to grip and hold a cartridge. More specifically, the gripping shoulder 35 is provided with a plurality of gripping teeth spaced circumferentially to provide a plurality of gaps (see FIG. 3A), each tooth having a triangular configuration with a proximally oriented pointed end, thereby creating a plurality of gaps having a distally oriented pointed configuration, this allowing the above-described distally facing pointed projections on the cartridge to be received between the teeth to thereby serve as a gripping means when the cartridge holding means has been moved into engagement with the cartridge. In this way an easy-to-use front loaded drug delivery device is provided which appears as a traditional rear loaded device and which is also actuated by rotational movement to mount and remove a cartridge, the resemblance providing for ease of acceptance and adaptation among users accustomed to traditional types of rear loaded drug delivery devices.

When it is time to mount a new cartridge the outer tube member is rotated e.g. 90 degrees by which action the gripping shoulders 35 are moved distally and slightly outwards, this allowing the mounted cartridge to be removed. For ease of operation the cartridge may be moved distally a certain distance as the shoulders are moved, e.g. by engagement with arms forming the gripping shoulders and/or by additional spring means providing a biasing distally directed force (see below). Depending on the design of the locking and actuation mechanism the gripping shoulders may be able to be left in the open position or they may be retracted automatically as the outer tube member is rotated backwards by return spring means. Whether or not a spring is provided the cartridge holder may be provided with locking means allowing the outer tube member to be securely parked in either the open or closed position, e.g. by a rotational snap lock. When a new cartridge is inserted the drive expelling means has to be in a state allowing a new cartridge with a proximally positioned piston to be inserted. An exemplary embodiment providing this functionality will be described below.

Figure 3A:
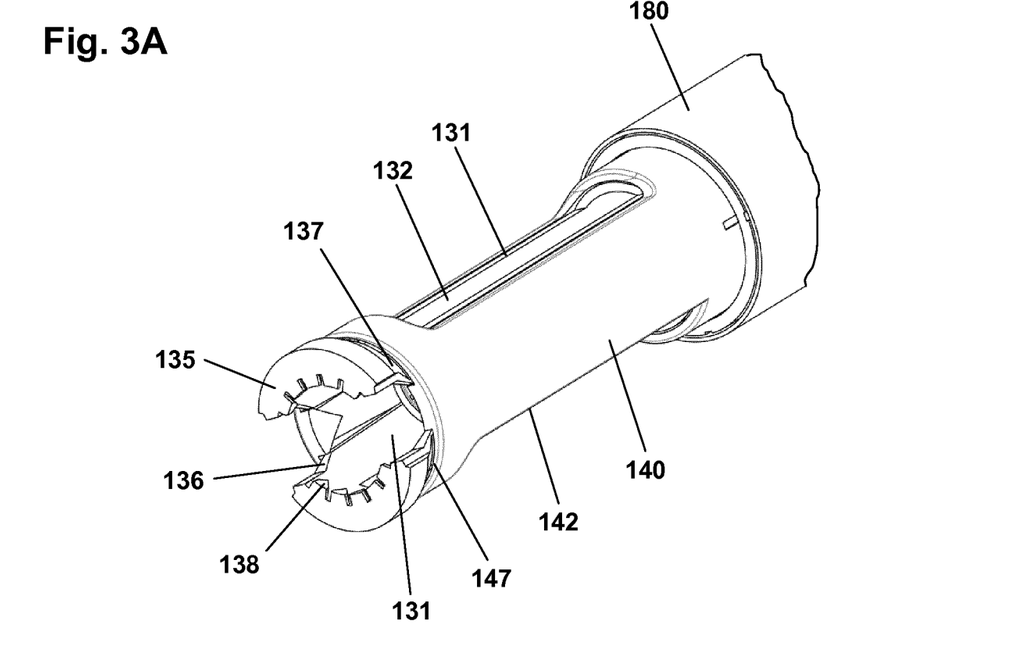
FIGS. 3A and 3B show detail views of a front-loaded cartridge holder in an open respectively closed state, the cartridge holder being of the type shown in FIG. 2 and may be used in combination with embodiments of the present invention.
Figure 3B:
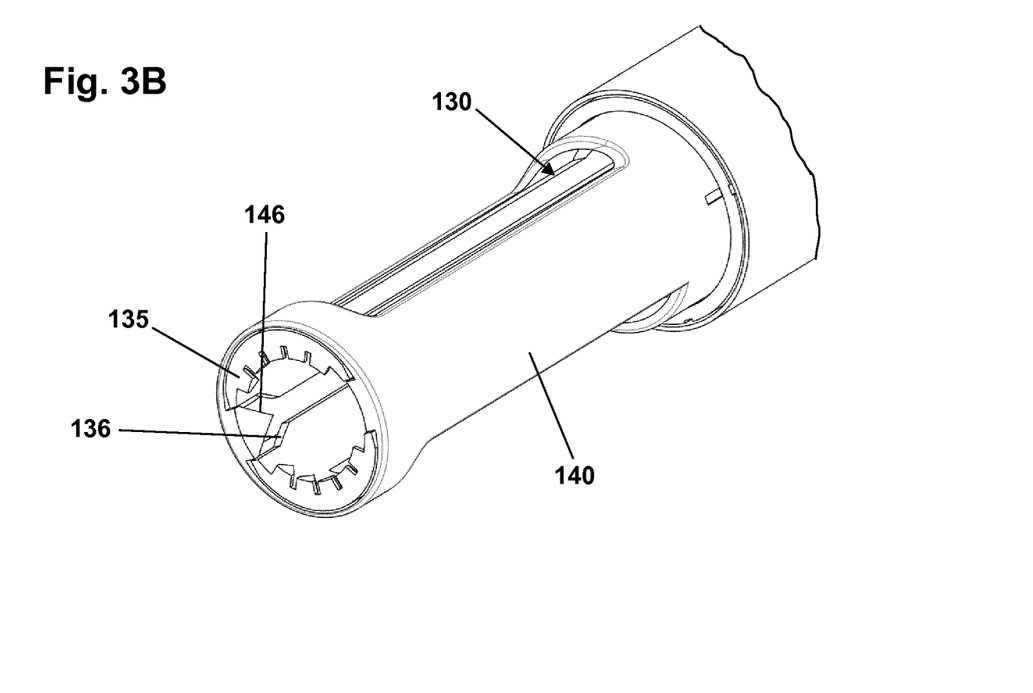

The mechanical arrangement providing the above-described user-interface, i.e. rotation of an outer tubular sleeve member moves gripping shoulders in and out, can be provided in numerous ways. Referring to FIGS. 3A and 3B a cartridge holder of the same front-loaded type as shown in FIG. 1 but having an alternative configuration, i.e. circular instead of oval, can be seen. The cartridge holder 130 comprises two opposed flexible arms 131 extending from a proximal ring portion arranged in axially guided sliding and thus non-rotational engagement with the outer tubular sleeve member 140, each arm being provided with a gripping shoulder 135. By this arrangement the gripping shoulders will rotate together with the outer tubular sleeve member and thus relative to the housing 180 as they are moved axially. In shown embodiment two opposed windows 132 are formed in the gripping member, one in each arm, each window being aligned with a corresponding window 142 formed in the outer tubular sleeve member, the two pairs of windows moving together in rotational alignment. Alternatively the gripping member and/or the outer tubular sleeve member may be manufactured fully or partly from a transparent material. Each gripping shoulder comprises an outer inclined and curved surface 137 adapted to engage a correspondingly curved distal actuation edge 147 of the outer tubular sleeve member 140, as well as a pair of inclined edge portions 136 adapted to engage a pair of corresponding inclined actuation surfaces 146 arranged on the inner surface of the actuation sleeve. By this arrangement the inclined actuation surfaces 36 will force the gripping shoulders outwardly to their open position as the actuation surfaces 136 are moved distally and into sliding contact with the sleeve actuation surfaces 146. Correspondingly, when the arms are moved proximally the outer curved surfaces 137 engage the actuation edges 147 and are thereby forced inwardly into their gripping position.

In alternative embodiments the gripping members may be arranged non-rotationally relative to the body portion, just as the actuation sleeve may be arranged to be moved axially only or by a combination of axial and rotational movement.

Figure 4:
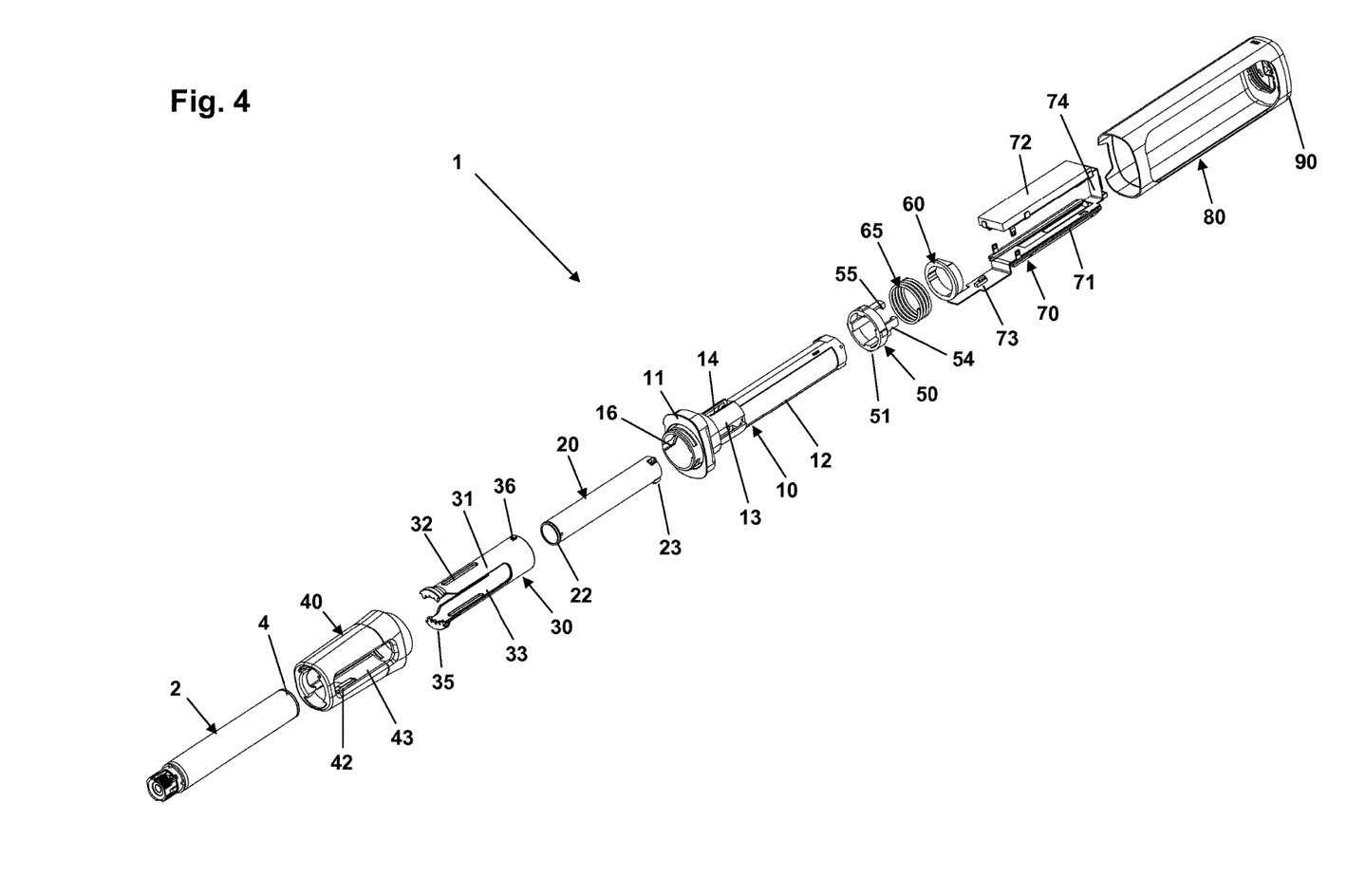
FIG. 4 shows in an exploded view components of the device shown in FIG. 2.

FIG. 4 shows an exploded view of the motorized drug delivery device 1 shown in FIG. 1. The device comprises a generally tubular chassis member 10, a generally cylindrical expelling assembly 11, a bias assembly comprising a bias member 50, a spring 65 and a spring support member 60, the device further comprising a control assembly 70, a generally tubular housing 80 with a proximal actuation button 90, and a cartridge holder assembly comprising an outer rotatable actuation sleeve 40 and an inner cartridge holder member 30.

The chassis comprises a distal coupling flange portion 11 for the cartridge holder assembly, a tubular proximal portion 12 adapted to receive and mount the expelling assembly, and an intermediate tubular portion 13 adapted to receive the proximal end of an inserted cartridge. The bias member comprises a distal ring portion 51 and a number of proximally extending leg portions 54 (here: four), each leg portion comprising at the distal end thereof a seat portion 55 extending radially inwards and being adapted to engage the proximal rim portion of an inserted cartridge. In a mounted position the bias member is arranged axially slidable around the intermediate tubular portion with the legs received in corresponding axial slots 14 formed therein, the seat portions thereby protruding into the interior of the intermediate portion. The spring support member is mounted axially fixed on the chassis, thereby allowing the spring to provide a distally directed biasing force on the bias member. The expelling assembly is in the form of a motor-in-piston assembly as described above comprising an interior motor and gear box drive assembly mounted axially and rotationally locked to the proximal end of the chassis, and an outer axially displaceable piston tube 20 with a distal drive head 22 adapted to engage the piston of a loaded cartridge, the piston tube comprising a number of proximal guide projections 23 adapted to non-rotationally engage corresponding guide means of the chassis. As also described above, the drive assembly comprises a cylindrical drive member provided with an exterior thread arranged in treaded engagement with a correspondingly threaded interior wall 21 of the piston tube (see FIG. 8), whereby rotation of the drive member results in axial non-rotational displacement of the piston tube. In FIG. 4 only the piston tube is shown, the motor-gear drive assembly being shown in FIG. 5 and described in greater detail below. The control assembly has a generally U-formed configuration with a first PCB portion 71 on which the majority of the electronic control components including a controller are arranged, and a second portion on which a rechargeable battery 72 is mounted The two portions are connected to each other by a proximal bridge portion 74 and are arranged opposed on each side of the chassis. A first "cartridge" switch 73 adapted to be controlled by the bias member (see below) is mounted on the PCB portion and a second switch adapted to be controlled by the proximal actuation button 90 is mounted on the bridge portion. The PCB portion is further connected to the LCD and input keys (not shown) as well as to sensor means arranged in the piston tube distal drive head 22 by means of a flexible PCB portion allowing axial movement there between (see below). The housing is mounted to the coupling flange portion 11.

Turning to the cartridge holder assembly, in an assembled state the cartridge holder member 30 is mounted rotationally locked but axially moveable inside the actuation sleeve 40 which is mounted axially locked but rotationally moveable to the chassis coupling flange portion 11. The actuation sleeve has an operational position in which the oval sleeve is rotated to be flush with the oval housing and the cartridge holder member is retracted to its operational closed holding position, and a loading/un-loading position in which the oval sleeve is rotated to be non-flush with the oval housing and the cartridge holder member is extended to an open loading position allowing a cartridge to be removed and replaced with a new.

The cartridge holder comprises a pair of opposed flexible arms 31 extending from a proximal ring portion, each arm being provided with a distal gripping portion 35 having a plurality of proximal facing gripping teeth spaced circumferentially to engage the above-described distally facing pointed projections on the cartridge. A pair of longitudinally oriented opposed slots 32 is formed in the arms, the slots each receiving a longitudinally oriented spline 42 formed on the inner surface of the actuation sleeve, this providing axially guided non-rotational engagement with the sleeve. Two opposed gaps (windows) 33 are formed between the cartridge holder arms, each window being aligned with a corresponding window 43 formed in the outer tubular sleeve, the two pairs of windows moving together in rotational alignment. Corresponding to the embodiment of FIG. 3B, when the actuation sleeve is rotated from operational position the gripping portions are moved distally and laterally to their open position. Movement of the cartridge holder member and the arms relative to the actuation sleeve is controlled by cooperating guide means arranged between the cartridge holder and/or chassis coupling flange portion. In the shown embodiment axial movement of the cartridge holder member is controlled by cartridge holder guide projections 36 received in corresponding flange portion guide tracks 16 and lateral movement of the distal gripping portion is controlled by corresponding inclined surfaces arranged distally on the cartridge holder respectively the actuation sleeve, i.e. similar to the arrangement shown in FIGS. 3A and 3B.

Figures 5, 6:
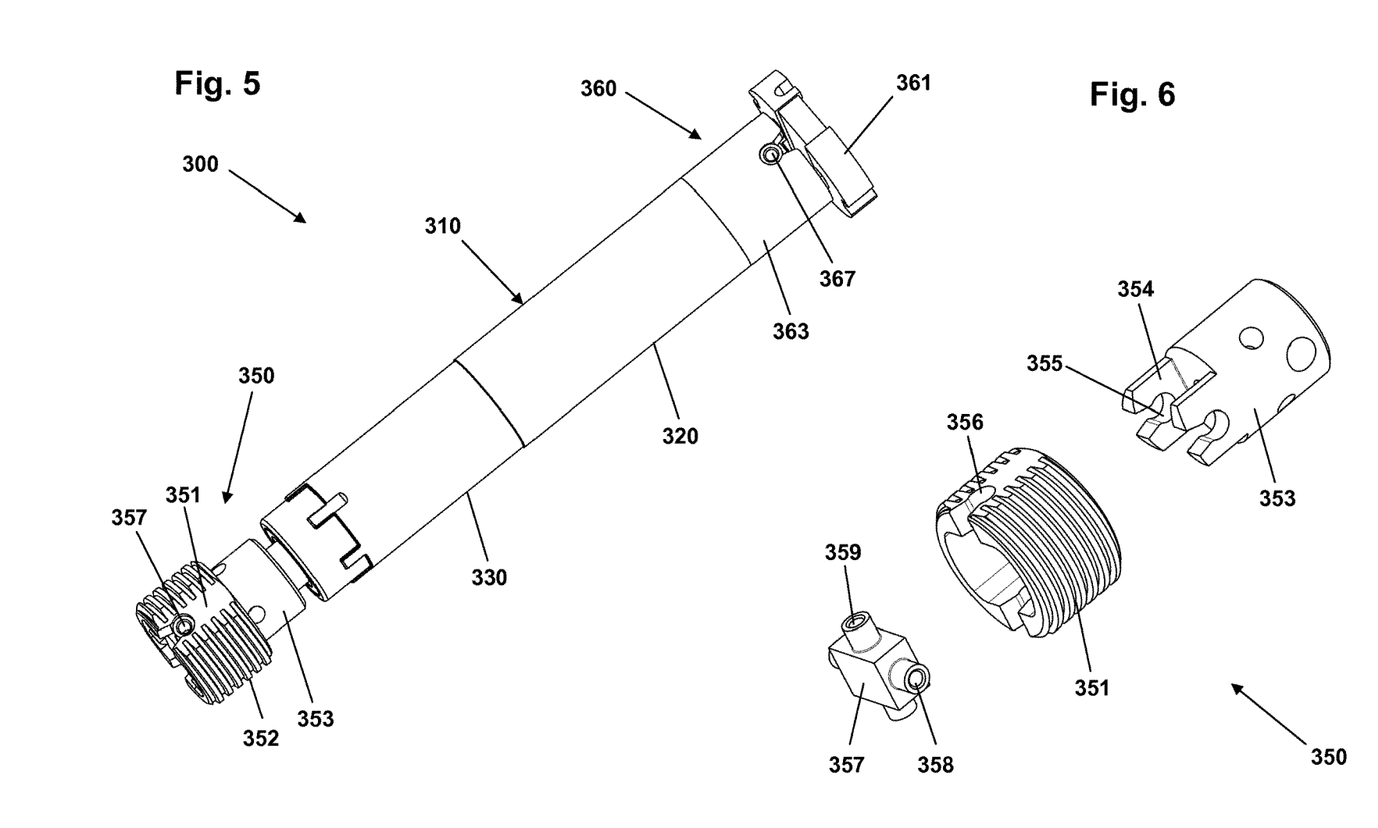
FIG. 5 shows the motor-gear assembly of the device shown in FIG. 2.
FIG. 6 shows in an exploded view components of the assembly shown in FIG. 5.

FIG. 5 shows the motor-gear drive assembly 300 not shown in FIG. 4. More specifically, the assembly 300 comprises a tubular main portion 310 composed of a proximal motor assembly 320 and a distal gearbox assembly 330 having a rotatable drive shaft 331 (see FIG. 7) defining a z-axis of rotation. Portions of the controller circuitry for controlling the motor may be incorporated in the motor assembly. The assembly further comprises a distal cylindrical drive member 351 having an outer thread adapted to be arranged in engagement with the piston drive tube inner thread. At the proximal end a disc-formed chassis connector 361 is arranged. Corresponding to the flexible joints described with reference to FIG. 1 the drive assembly 300 is provided with flexible joints in the form of a distal universal joint 350 arranged between the drive shaft and the drive member and a proximal universal joint 360 arranged between the motor assembly proximal portion and the chassis tube proximal portion.

It should be noted that the drive assembly of FIG. 5, together with the drive tube shown e.g. in FIG. 4, also represents a general purpose telescopic drive assembly in its own right, and which may be used in many other designs in which a compact and reliable telescopic drive assembly is relevant.

Turning to FIG. 6 the distal universal joint 350 is shown in greater detail. Whereas a traditional universal joint (or cardan joint) is arranged and designed to provide a joint between two axle portions spaced apart axially, the shown universal joint comprises an input member arranged partly inside an outer output member. More specifically, the universal joint arrangement comprises an input member in the form of a tubular axle connector 353 adapted to be mounted non-rotationally on the drive shaft, a tubular output member in the form of the externally threaded drive member 351, as well as a cross member 357 connecting the input and output members. The axle connector comprises a pair of distally extending opposed flanges 354 each having a hinge seat 355 adapted to receive a hinge pin. The drive member comprises at the distal end a pair of opposed hinge seats 356 adapted to receive a pair of hinge pins. The cross member comprises a first pair of opposed laterally projecting hinge pins 358 adapted to be received by snap action in the hinge seats 355 of the axle connector, as well as a second pair of opposed laterally projecting hinge pins 359 adapted to be received by snap action in the hinge seats 356 of the drive member, the first and second pair of hinge pins being off-set 90 degrees relative to each other, thereby in combination providing a universal joint.

In contrast to the distal universal joint the proximal universal joint 360 does not rotate during operation of the drive assembly. The proximal universal joint comprises a tubular motor assembly connector 363 adapted to be mounted non-rotationally to the motor assembly proximal end, a disc-formed chassis connector 361 adapted to be mounted non-rotationally in the chassis tube proximal end, as well as a cross member 367 connecting the two connectors to form a universal joint. The components of the proximal joint comprises pins and seats corresponding to the distal joint with the difference that the two connector members are arranged axially next to each other.

By providing a drive assembly with universal joints as described above, the motor-gear drive assembly 300 is allowed to move, e.g. flex or "wobble", relative to the chassis, just as the drive member 351 together with the drive tube 20 is allowed to move, e.g. flex or "wobble", relative to the motor-gear drive assembly and thus also the chassis, the arrangement yet still providing the desired transmission of rotation, this allowing a cost-effective design requiring less restrictive tolerances for the involved components.

Figure 7:
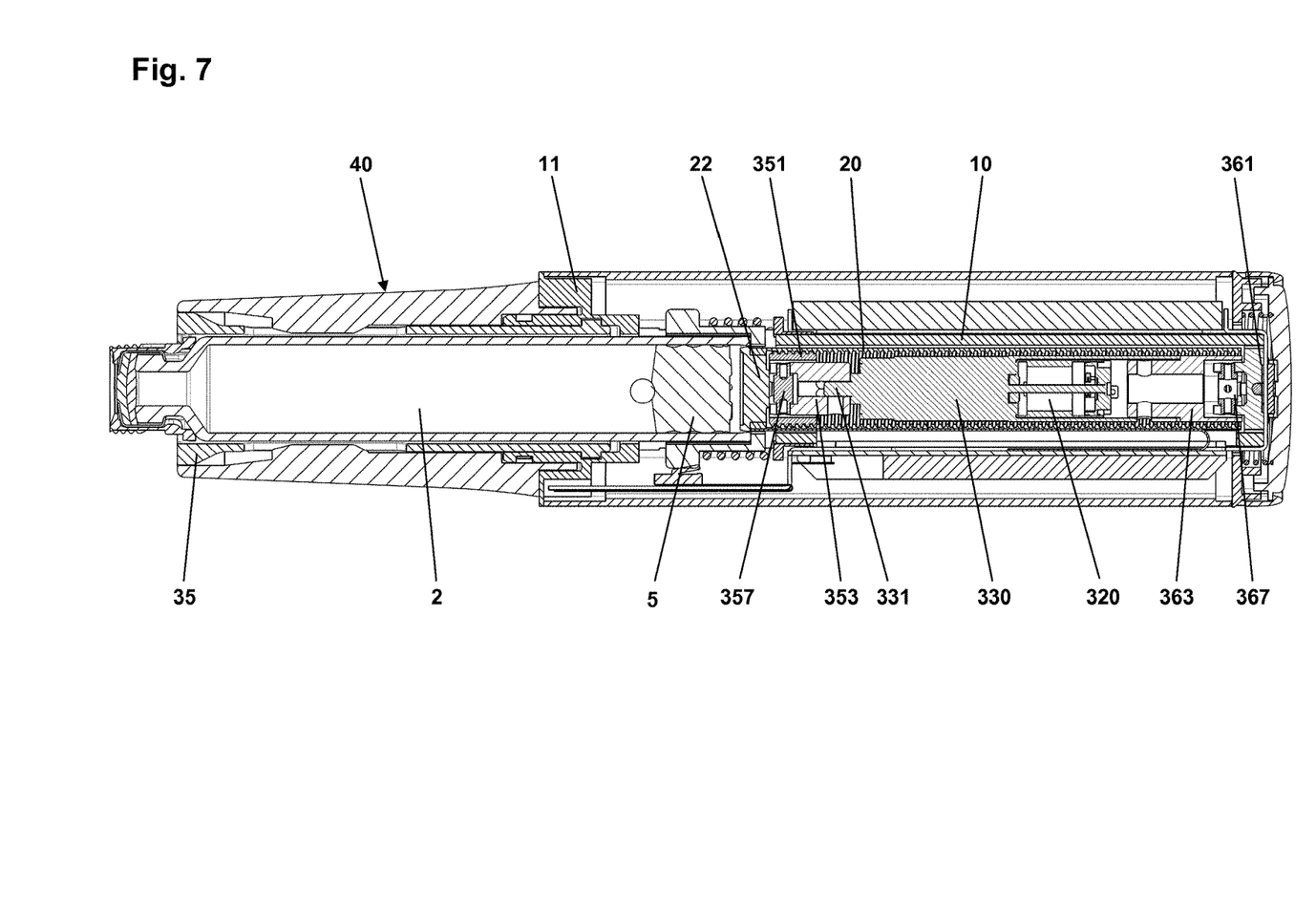
FIG. 7 shows a cross-sectional view of the drug delivery device of FIG. 2, and FIGS. 8-10 show cross-sectional views of the drug delivery device of FIG. 2 in different operational states, the motor-gear assembly being removed.

FIG. 7 shows a cross-sectional view of the drug delivery device of FIG. 1 in which the drive assembly with the two universal joints as described above can be seen. The features of the device are described in greater detail below with reference to FIG. 8.

Figure 8:
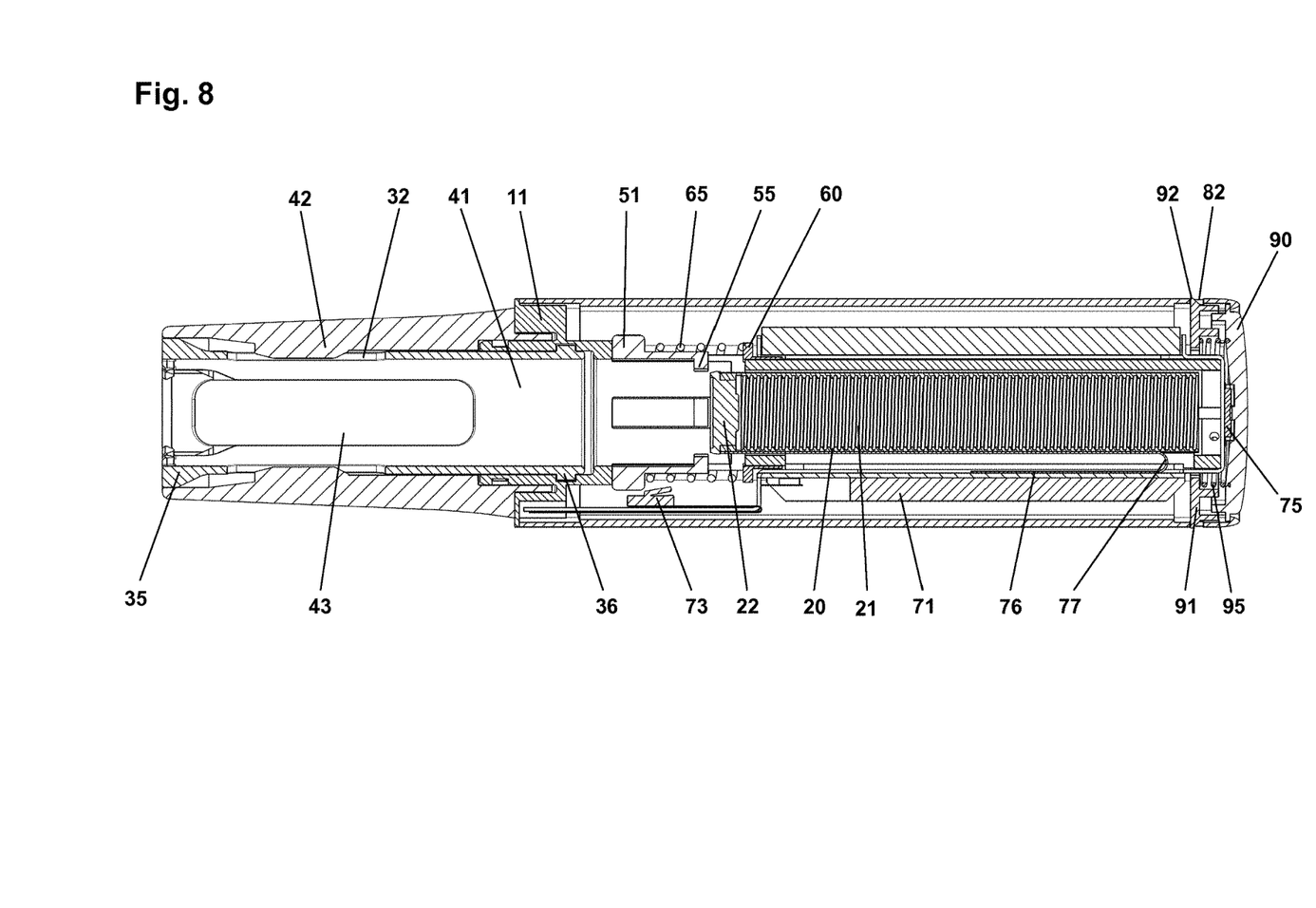
Figure 9:
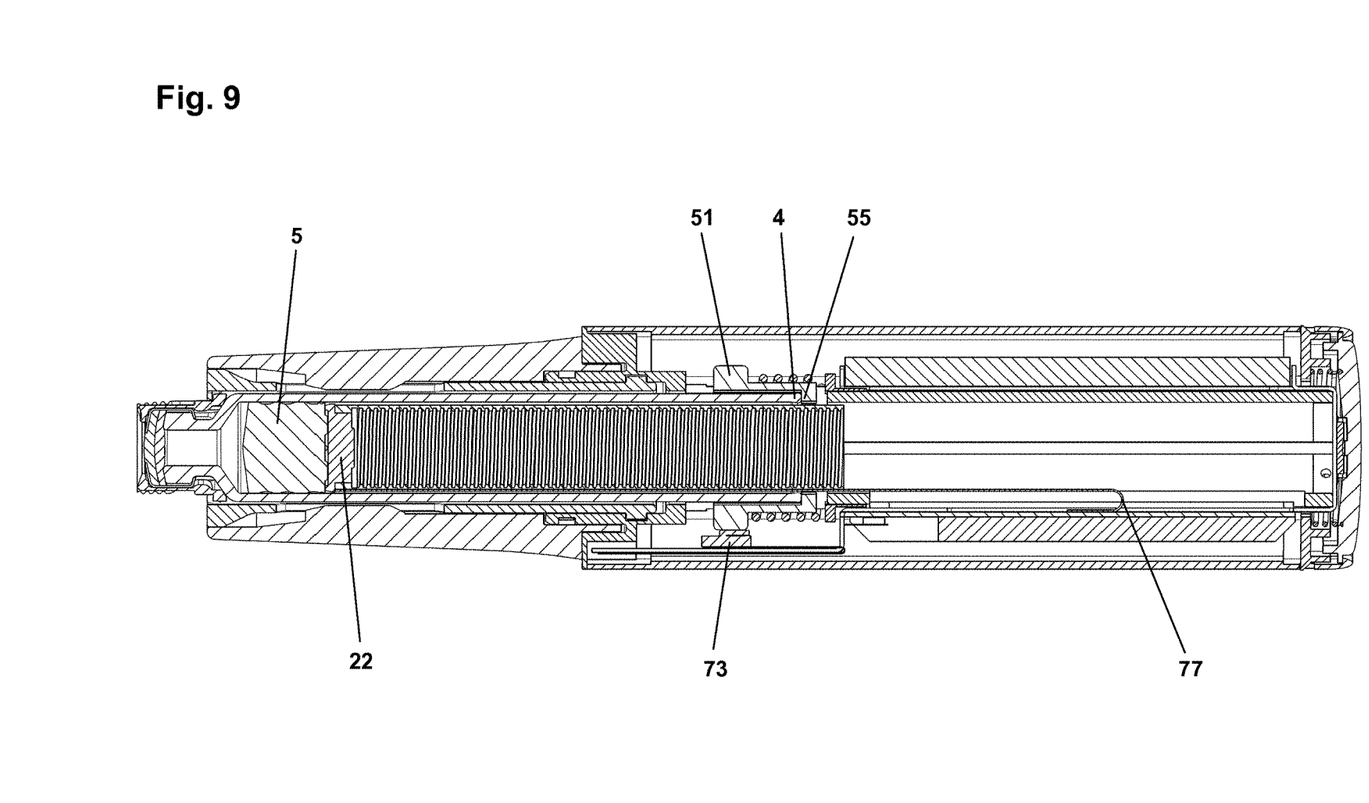
Figure 10:
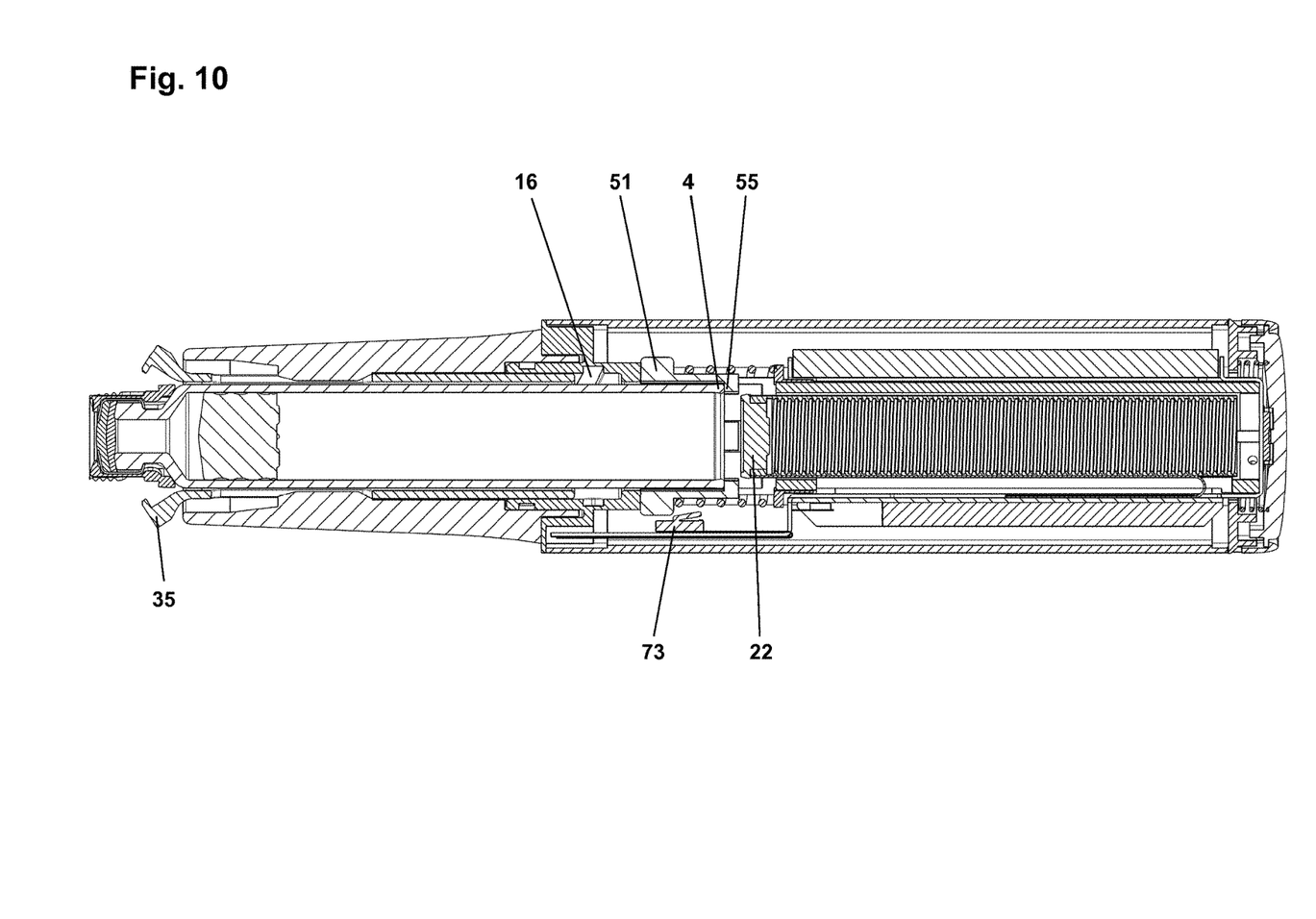

Turning to FIGS. 8-10 cross-sectional views of the drug delivery device 1 of FIGS. 2 and 4 are shown in different operational states, FIG. 8 showing the device in an initial empty state in which the cartridge holder is closed and the piston tube is fully retracted. In all FIGS. 8-10 the expelling assembly is in form of the piston tube only, the motor and gear box drive assembly being omitted for clarity reasons.

More specifically, FIG. 8 shows the bias member 50 moved to a distal-most position in which the distal ring portion 50 abuts a corresponding stop surface on the chassis, the seat portions 55 being free. The actuation sleeve 40 is rotated to its operational position and the cartridge holder member 30 is retracted to its closed position. As appears, with the bias member in its distal-most position the cartridge switch 73 is in its non-actuated state, this indicating to the control electronics that no cartridge is loaded. Correspondingly, the piston tube is positioned in its retracted position. As appears, when the cartridge holder assembly is actuated to its open position the bias member is not moved and the cartridge switch remains un-actuated.

A number of further details can be seen in FIG. 8. The button 90 is received in the housings proximal opening and supported by an annular support member 91 locked to the housing by projections 92 engaging corresponding openings 82 in the housing. A spring 95 providing a proximally directed biasing force on the button is arranged between the button and the support. The above-described second switch 75 adapted to be controlled by the proximal actuation button can be seen mounted on the bridge portion. A flexible ribbon 76 with a plurality of conductors is arranged with a U-bend 77 between the PCB portion 71 and the sensors (not shown) arranged in the piston head, this allowing the piston tube and piston head to travel axially with the U-bend moving correspondingly.

Turning to FIG. 9, the device can be seen with a mounted cartridge and the piston pushed to an almost distal-most position by the piston tube. Before this state has been reached the following has happened as compared to the state of FIG. 4. When the user desires to load a cartridge the actuation sleeve is rotated to its loading/un-loading position and the cartridge holder gripping shoulders are moved to their open position (see FIG. 10). As mentioned above, the bias member does not move. The user then inserts a new cartridge in the cartridge holder through the distal opening until the cartridge proximal rim seats against the seat fingers 55 of the bias member. Due to the bias of the spring the user is informed that the cartridge has been initially fully inserted and should not be pushed further proximally. Subsequently the user rotates the actuation sleeve back to its operational state resulting in the gripping shoulders moving inwards and proximally thereby retracting the cartridge to its fully inserted position, thereby also moving the bias member proximally against the bias of the spring, this resulting in the cartridge switch 73 being actuated. The actuation of the cartridge switch from open to closed signals to the device controller that two actions can be assumed to have taken place: (i) a cartridge has been inserted and (ii) the cartridge holder has been closed, this initiating that the drive head is moved distally into contact with the cartridge piston. In the shown embodiment it is contemplated that detection of contact between the drive head and the piston is detected by electronic sensor means arranged in the drive head, e.g. using proximity detection as disclosed in WO 2013/144152. Alternatively contact could be detected by monitoring the load on the motor, e.g. by monitoring the current. The device has now been primed and is ready for use during which the piston will be moved distally until the cartridge has been emptied as shown in FIG. 9. As appears, the U-bend portion 77 of the flexible connector has also moved distally.

As appears from the above description of a normal loading procedure, the priming motor control is based on the assumption that the cartridge has been moved to its fully loaded position by closing the cartridge holder. However, in case the user during cartridge insertion forces the cartridge proximally against the bias of the spring, the bias member will be moved proximally and actuate the cartridge switch. As it can be assumed that this actuation is not intended by the user, piston tube advancement may be delayed a few seconds awaiting the user closing the cartridge holder properly.

Turning to FIG. 10, the device can be seen with the cartridge holder open and with an empty cartridge pushed distally by the bias member, and with the piston tube moved to its retracted position. Before this state has been reached the following has happened as compared to the state of FIG. 5. When the user desires to remove a cartridge (which may be fully or partly empty), the user rotates the actuation sleeve to its loading/un-loading position whereby the cartridge holder gripping shoulders are moved to their open position, this allowing the cartridge to be pushed proximally by the distally directed biasing force of the bias member. To prevent that the cartridge "shoots out" or slides out of the cartridge holder, a slight friction may be provided between the cartridge holder and a loaded cartridge. As the bias member is moved distally by the spring the bias member disengages the cartridge switch. The actuation of the cartridge switch from closed to open signals to the device controller that two actions can be assumed to have taken place: (i) the cartridge holder has been opened and (ii) an inserted cartridge has been pushed distally by the bias member, this initiating retraction of the piston tube to its fully retracted position as seen in FIG. 10. As it will take some time to retract the piston tube the user will normally remove the cartridge before the piston tube has been fully retracted, however, as the piston tube in all positions are positioned fully inside the cartridge holder it is protected against unintended damage as would be the case if it projected from the device after a traditional rear-loaded cartridge holder had been removed from the main part. During normal use situations it can be assumed that the piston tube is fully retracted when the user inserts a new cartridge, however, to prevent a "too fast" insertion of a new cartridge the user may be instructed to await a signal indicating that the device is ready to receive a cartridge, e.g. a sound signal.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device, comprising:
a compartment adapted to receive and hold a drug-filled cartridge having an axially moveable piston,
a support structure,
a drive tube comprising an inner thread,
a motor assembly having a distal portion and a proximal portion, the distal portion comprising a rotatable drive shaft and being adapted to be received inside the drive tube,
a drive member comprising an outer thread, and
a controller for controlling the motor assembly,
wherein:
the drive member outer thread is in threaded engagement with the drive tube inner thread,
the motor assembly is arranged non-rotational relative to the support structure,
the drive tube is arranged axially displaceable but non-rotational relative to the motor assembly and is adapted to engage and axially move, directly or indirectly, the piston of a loaded cartridge to thereby expel drug from the cartridge,
the motor assembly proximal portion is connected to the support structure via a first flexible joint, and
the drive shaft is connected to the drive member via a second flexible joint,
whereby rotation of the drive shaft results in axial, non-rotational displacement of the drive tube relative to the support structure.

2. The drug delivery device as in claim 1, wherein:
the drive shaft defines a general axis, and
the first and second flexible joints are configured to prevent rotation and axial movement relative to the general axis between the motor assembly proximal portion and the support structure respectively between the drive shaft and the drive member.

3. The drug delivery device as in claim 1, wherein each of the flexible joints is in the form of a universal joint, a helical spring or an Oldham coupling.

4. The drug delivery device as in claim 1, wherein the drive tube and the support structure comprises cooperating guide structures providing that the drive tube is axially displaceable but non-rotational relative to the support structure.

5. The drug delivery device as in claim 1, wherein the controller and motor assembly is adapted to move the drive tube in a distal direction to thereby expel drug from a loaded cartridge, and move the drive tube in an opposed proximal direction to thereby retract the drive tube from a loaded cartridge.

6. The drug delivery device as in claim 1, further comprising setting structure allowing a user to set a dose of drug to be expelled.

7. The drug delivery device as in claim 1, comprising:
a rechargeable electric power source, and
an electrical connector allowing an external connector of a power source to be connected for recharging the power source,
wherein the controller is adapted to detect a condition indicative of an external power source being connected to the electrical connector and subsequently disable the expelling assembly to thereby prevent that drug can be expelled from a loaded cartridge when an external power source has been connected to the electrical connector.

* * * * *